United States Patent [19]

Matsumoto et al.

[11] 4,320,227
[45] Mar. 16, 1982

[54] PROCESS FOR PRODUCING METHACROLEIN AND METHACRYLIC ACID

[75] Inventors: Mutsumi Matsumoto; Kouichi Wada, both of Takasaki, Japan

[73] Assignee: Nippon Kayaku Kabushiki Kaisha, Tokyo, Japan

[21] Appl. No.: 109,554

[22] Filed: Jan. 4, 1980

[30] Foreign Application Priority Data

Jan. 23, 1979 [JP] Japan .................................. 54-5584
Jan. 26, 1979 [JP] Japan .................................. 54-7192

[51] Int. Cl.$^3$ ..................... C07C 45/65; C07C 47/22; C07C 51/235; C07C 57/05
[52] U.S. Cl. ................................ 562/534; 252/435; 252/437; 562/535; 568/459
[58] Field of Search ............................. 562/535, 534; 260/601 R; 252/435, 437; 568/459

[56] References Cited

U.S. PATENT DOCUMENTS 3,998,877 12/1976 Ada et al. ............................ 562/535
4,001,316 1/1977 Ishimi .................................. 562/535

FOREIGN PATENT DOCUMENTS 149611 11/1975 Japan ................................... 562/535

*Primary Examiner*—Vivian Garner
*Attorney, Agent, or Firm*—Russell and Nields

[57] ABSTRACT

A process for producing methacrolein and methacrylic acid by oxidizing isobutyl aldehyde with molecular oxygen or molecular oxygen-containing gas in the vapor phase characterized by the use of a catalyst of heteropoly-acid or a mixture of heteropoly-acid and its salt which has the general formula:

$$Mo_aV_bP_cX_dY_eO_f$$

wherein Mo, V, P and O represent respectively molybdenum, vanadium, phosphorus and oxygen, X represents one or more elements selected from the group consisting of copper, tin, thorium, aluminum, germanium, nickel, iron, cobalt, zinc, titanium, lead, rhenium, zirconium, cerium, chromium, bismuth and arsenic, Y represents one or more elements selected from the group consisting of potassium, rubidium, cesium and thallium and a, b, c, d, e and f represent the atomic ratio of the elements where, a is 10,
b is a number of 6 or less than 6 excluding 0,
c is a number of 0.5 to 6,
d is a number of 3 or less than 3 excluding 0,
e is a number of 0 to 0.8,
f is a number determined depending on the valency and atomic ratio of other elements.

4 Claims, No Drawings

PROCESS FOR PRODUCING METHACROLEIN AND METHACRYLIC ACID

DETAILED DESCRIPTION OF THE INVENTION

This invention relates to a process for producing methacrolein and methacrylic acid by oxidizing isobutyl aldehyde with molecular oxygen or molecular oxygen-containing gas in the vapor phase.

Many processes have been proposed for the production of methacrylic acid which is a raw material of methyl methacrylate. Most of the processes are those where isobutylene is used as a raw material and it is oxidized to methacrolein, and then methacrolein is oxidized to methacrylic acid.

The processes using isobutyl aldehyde as a raw material have been proposed too. However, most of the processes are those where isobutyl aldehyde is oxidized to isobutyric acid in the first step and then isobutyric acid is converted to methacrylic acid in the other step.

There are also some other proposed processes where isobutyl aldehyde is oxidized to methacrolein and methacrylic acid. But, in these processes, the yield of the product is not good and the life of the catalyst used in these processes is short.

The inventors of the present application have made an earnest study on eliminating the defects of the processes and accomplished this invention.

According to the present invention, methacrolein and methacrylic acid can be obtained from isobutyl aldehyde in high yield for a long time. Particularly, methacrylic acid can be obtained in high yield. The catalyst used in the present invention has high activity, high selectivity, as well as very long catalyst life.

This invention relates to a process for producing mathacrolein and methacrylic acid by oxidizing isobutyl aldehyde with molecular oxygen or molecular oxygen-containing gas in the vapor phase characterized by the use of a catalyst of heteropoly-acid or a mixture of heteropoly-acid and its salt which has the general formula:

$$Mo_aV_bP_cX_dY_eO_f$$

wherein Mo, V, P and O represent respectively molybdenum, vanadium, phosphorus and oxygen, X represents one or more elements selected from the group consisting of copper, tin, thorium, aluminum, germanium, nickel, iron, cobalt, zinc, titanium, lead, rhenium, zirconium, cerium, chromium, bismuth and arsenic, Y represents one or more elements selected from the group consisting of potassium, rubidium, cesium and thallium and a, b, c, d, e and f represent the atomic ratio of the elements where, a is 10, b is a number of 6 or less than 6 excluding 0 and, preferably, 0.5 to 3, c is a number of 0.5 to 6 and, preferably, 0.5 to 3, d is a number of 3 or less than 3 excluding 0 and, preferably, 0.01 to 1.0, e is a number of 0 to 0.8 and, preferably, 0 to 0.5, f is a number determined depending on the valency and atomic ratio of other elements and is usually a number of 35 to 80.

In this invention, the preferred catalyst is the one represented by the following formula:

$$Mo_{a'}V_{b'}P_{c'}Cu_{d'}X'_{e'}Y'_{f'}O_{g'}$$

wherein, Mo, V, P, Cu and O represent respectively molybdenum, vanadium, phosphorus, copper and oxygen, X' represents one or more elements selected from the group consisting of arsenic, thorium, aluminum, germanium, nickel, iron, cobalt, zinc, titanium, lead, rhenium, zirconium, cerium, bismuth, tin and chromium, Y' represents one or more elements selected from the group consisting of potassium, rubidium, cesium and thallium and a', b', c', d', e', f' and g' represent the atomic ratio of the elements where, a' is 10, b' is a number of 6 or less than 6 excluding 0 and, preferably, 0.5 to 3, c' is a number of 0.5 to 6 and, preferably, 0.5 to 3, d' is a number of 3 or less than 3 excluding 0 and, preferably, 0.01 to 1.0, e' is a number of 3 or less than 3 excluding 0 and, preferably, 0.01 to 1.0, $d'+e'$ is a number of 3 or less than 3 excluding 0, f' is a number of 0 to 0.8 and, preferably, 0 to 0.5, g' is a number determined depending on the valency and atomic ratio of other elements and is usually a number of 35 to 80.

The basic structure of the catalyst of the present invention is phosphovanadomolybdic acid. In case Y element is not present, the catalyst of the present invention is a catalyst in which a part of the catalyst-structure formed by the phosphovanadomolybdic acid is occupied by X element. In case Y element is present, the catalyst of the present invention is a catalyst in which a part of the catalyst-structure formed by the coexistence of phosphovanadomolybdic acid and its Y-metal salt is occupied by X element.

As mentioned above, in case Y element is not present, the catalyst is heteropoly-acid composed mainly of phosphovanadomolybdic acid, and in case Y element is present, the catalyst is a mixture of heteropoly-acid composed mainly of phosphovanadomolybdic acid, and its Y-metal salt. X element occupies a part of the structure of heteropoly-acid and its salt, if present.

In the X-ray diffraction pattern of the catalyst used in the present invention, the peaks of $2\theta=8.0°$, 8.9°, 9.3°, etc. characteristic diffraction peaks of the heteropoly-acid are observed. Further, in case heteropoly-acid salt is present, the peaks of $2\theta=26.6°$, 10.8°, etc. characteristic diffraction peaks of the Y-metal salt of the heteropoly-acid are also observed. However, in the region of the catalyst in which the amount of coexisting salt is poor, only the peaks due to the acid are observable. The catalyst in which the amount of Y-component is too much, to the extent in that particularly only the peaks due to Y-salt of the heteropoly-acid are observed does not give good results. It is essential to control the amount of addition of Y-component within the range of the present invention.

Although the catalyst used in the present invention is heteropoly-acid or a mixture of heteropoly-acid and its salt, it may additionally contain other compounds such as oxides of the constituent element.

The catalyst of this invention is excellent for industrial use since it has high activity, high selectivity, as well as very long catalyst life. Further, according to this invention, the reaction can be conducted at a high space velocity, because the increase in the space velocity has no substantial effects on the results of the reaction where the catalyst of this invention is employed. The catalyst of this invention is water soluble, which provides additional advantages in that it can easily be carried on a carrier and regenerated also with ease by dissolving it again in water after being deactivated in a long use for the reaction.

While the catalyst of this invention can be prepared by general methods for preparing usual heteropoly-acid, and its Y-metal salt, it should particularly be noted to avoid the formation of a heteropoly-acid ammonium salt structure in the resultant catalyst.

The catalyst of this invention can be prepared, for example, in the following manner. The catalyst of this invention can be prepared by reacting the starting materials of the constituent elements in water or in an organic solvent, an evaporating to dryness.

Particularly preferred preparation methods include those such as dispersing or dissolving the starting material, for example, oxides or phosphates of the constituent elements into water, reacting the same under heating while optionally adding hydrogen peroxide, removing insoluble component if necessary, and then evaporating the solution to dryness, or reacting phosphovanadomolybdic acid with oxides, hydroxides, phosphates, carbonates and the like of other constituent elements.

Various substances can be used as the starting material for the constituent elements of the catalyst.

The starting materials usable for the molybdenum component include, for example, molybdenum trioxide, molybdic acid or its salt, heteromolybdic acid or its salts, molybdenum metal and the like.

The starting materials usable for the phosphorus component include orthophosphoric acid, phosphorous acid, hypophosphorous acid or the salts thereof, diphosphorus pentoxide and the like.

The starting materials usable for the vanadium component include vanadium pentoxide, vanadium oxalate, vanadium sulfate, vanadic acid or its salts, phosphovanadomolybdic acid or its salt, vanadium metal and the like.

The starting materials usable for the components X and Y include corresponding oxides, phosphates, nitrates, sulfates, carbonates, molybdates, salts of organic acids, halides, hydroxides, metals of the elements X and Y and the like.

While the catalyst according to this invention exhibits high catalytic activity as it is, preferable effects such as improvements in thermal stability and catalyst life and increase in yield of methacrolein and methacrylic acid can be expected by carrying it on a suitable carrier. Preferred carriers include silicon carbide, α-alumina, aluminum powder, diatomaceous earth, titanium oxide and the like. The active carriers which react with heteropoly-acid are not preferable.

The calcination process which is required in most cases is not required when preparing the catalyst of this invention. Therefore, the catalyst of this invention can be prepared with ease and the price of the catalyst can be reduced.

The reactants used for the oxidation reaction in this invention are isobutyl aldehyde and molecular oxygen or molecular oxygen-containing gas, wherein the molar ratio of oxygen to isobutyl aldehyde preferably lies between 0.5 and 20 and, more preferably, between 1 and 10.

It is preferable to add water vapor to the feed gas in an amount between 1 and 20 and, more preferably, between 2 and 15 by molar ratio based on isobutyl aldehyde.

The feed gas may further contain other inert gases, for example, nitrogen, carbon dioxide, saturated hydrocarbon or the like.

The reaction temperature is preferably between 250°–400° C., more preferably, 250°–370° C.

The amount of the feed gas is preferably between 100 and 6000 $hr^{-1}$ and, more preferably, between 400 and 3000 $hr^{-1}$ as space velocity (SV) based on the NTP standard. Since the increase in the space velocity (SV) has no substantial effect on the results of the reaction where the catalyst of this invention is employed, the reaction can be conducted at a high space velocity.

While the reaction of this invention can be effected at a pressure either above or below the atmospheric pressure, it is suitably effected generally at a pressure near the atmospheric pressure. The preferred pressure for the reaction in this invention lies between 1 and 5 atm.

The reaction of this invention can be effected in any desired type of reactor such as of a fixed bed, a fluidized bed or a moving bed type.

In the following examples, no particular references are made to the details of oxygen in the catalyst composition since they are determined in accordance with the atomic ratio and valency of other elements.

The conversion of isobutyl aldehyde, the yield of methacrolein, the yield of methacrylic acid and the selectivity to (methacrolein+methacrylic acid) are defined as follows:

Conversion of isobutyl aldehyde (%) = 
$$\frac{\text{isobutyl aldehyde reacted (mol)}}{\text{isobutyl aldehyde supplied (mol)}} \times 100$$

Yield of methacrolein (%) = 
$$\frac{\text{methacrolein resulted (mol)}}{\text{isobutyl aldehyde supplied (mol)}} \times 100$$

Yield of methacrylic acid (%) = 
$$\frac{\text{methacrylic acid resulted (mol)}}{\text{isobutyl aldehyde supplied (mol)}} \times 100$$

Selectivity to (methacrolein + methacrylic acid) (%) = 
$$\frac{\text{Yield of methacrolein + Yield of methacrylic acid}}{\text{Conversion of isobutyl aldehyde}} \times 100$$

EXAMPLE A1

100 g of molybdenum trioxide, 6.3 g of vanadium pentoxide, 1.1 g of copper oxide and 8.0 g of orthophosphoric acid were dispersed or dissolved into 1000 ml of deionized water. The resultant mixture was boiled and refluxed with stirring for about 6 hours to produce a clear orange red solution. After removing a slight amount of insoluble contents, it was evaporated to dryness on a hot bath. The dried product thus obtained (catalyst) had a composition: $Mo_{10}V_1P_1Cu_{0.2}$ and was confirmed to be heteropoly-acid by the observation of X-ray diffraction peaks at $2\theta=8.0°$, 8.9°, 9.3° and the like. It was ground to 24–48 mesh and diluted with the same amount of quartz sands having the same size in mesh and then charged into a tubular reactor made of glass of 18 mm in inside diameter and the reactor was immersed in a fluidized bath. The feed gas of a composition wherein isobutyl aldehyde:oxygen:nitrogen:water vapour = 1:2.5:10:7 (in molar ratio) was passed through the tubular reactor at $SV=1000$ $hr^{-1}$ (NTP standard) and subjected to oxidation reaction at a reaction temperature of 325° C. for 60 days. The results are shown in Table A-1.

After the reaction of 60 days, X-ray diffraction anaysis of the catalyst was made and it was confirmed that molybdenum trioxide had not been formed and the structure of the catalyst has not changed.

EXAMPLES A2–A17

1.1 g of copper oxide in Example A1 was replaced in each of the examples with 1.6 g of tin oxide, 3.7 g of thorium oxide, 0.7 g of aluminum oxide, 1.4 g of germanium oxide, 1.0 g of nickel oxide, 1.1 g of iron oxide, 1.1 g of cobalt oxide, 1.1 g of zinc oxide, 1.1 g of titanium oxide, 3.2 g of trilead tetroxide, 3.4 g of rhenium oxide, 1.7 g of zirconium oxide, 2.4 g of cerium oxide, 1.4 g of chromium oxide, 3.2 g of bismuth oxide and 1.9 g of arsenic acid respectively and dried products (catalysts) having compositions as shown in Table A-1 were obtained. The dried products thus obtained were confirmed to be heteropoly-acid by the observation of X-ray diffraction peaks at $2\theta = 8.0°$, 8.9°, 9.3° and the like.

A series of continuous reactions were conducted using the above catalysts under the same reaction conditions as in Example A1. The results are as shown in Table A-1.

After the reaction of 60 days, X-ray diffraction analysis of the catalysts was made and it was confirmed that the structure of the catalysts had not changed.

TABLE A-1

| Example | Catalyst composition | Time on stream (days) | Reaction temperature (°C.) | Conversion of isobutyl aldehyde (%) | Yield of methacrolein (%) | Yield of methacrylic acid (%) | Selectivity to (methacrolein + methacrylic acid) (%) |
|---|---|---|---|---|---|---|---|
| A1 | $Mo_{10}V_1P_1Cu_{0.2}$ | 1 | 325 | 100 | 19.6 | 58.0 | 77.6 |
| | | 60 | 325 | 100 | 19.7 | 59.2 | 78.9 |
| A2 | $Mo_{10}V_1P_1Sn_{0.2}$ | 1 | 330 | 100 | 15.5 | 54.5 | 70.0 |
| | | 60 | 330 | 100 | 15.2 | 54.8 | 70.0 |
| A3 | $Mo_{10}V_1P_1Th_{0.2}$ | 1 | 330 | 100 | 19.5 | 53.5 | 73.0 |
| | | 60 | 330 | 100 | 19.6 | 53.7 | 73.3 |
| A4 | $Mo_{10}V_1P_1Al_{0.2}$ | 1 | 330 | 100 | 15.8 | 55.1 | 70.9 |
| | | 60 | 330 | 100 | 16.0 | 55.4 | 71.4 |
| A5 | $Mo_{10}V_1P_1Ge_{0.2}$ | 1 | 330 | 100 | 13.1 | 55.9 | 69.0 |
| | | 60 | 330 | 100 | 13.0 | 56.5 | 69.5 |
| A6 | $Mo_{10}V_1P_1Ni_{0.2}$ | 1 | 330 | 100 | 20.1 | 52.1 | 72.2 |
| | | 60 | 330 | 100 | 21.1 | 53.1 | 74.2 |
| A7 | $Mo_{10}V_1P_1Fe_{0.2}$ | 1 | 330 | 100 | 16.6 | 53.9 | 70.5 |
| | | 60 | 330 | 100 | 16.7 | 53.9 | 70.6 |
| A8 | $Mo_{10}V_1P_1Co_{0.2}$ | 1 | 330 | 100 | 17.2 | 53.0 | 70.2 |
| | | 60 | 330 | 100 | 17.5 | 53.5 | 71.0 |
| A9 | $Mo_{10}V_1P_1Zn_{0.2}$ | 1 | 335 | 100 | 18.1 | 51.5 | 69.6 |
| | | 60 | 335 | 100 | 18.5 | 51.8 | 70.3 |
| A10 | $Mo_{10}V_1P_1Ti_{0.2}$ | 1 | 330 | 100 | 15.1 | 54.8 | 69.9 |
| | | 60 | 330 | 100 | 15.3 | 55.0 | 70.3 |
| A11 | $Mo_{10}V_1P_1Pb_{0.2}$ | 1 | 330 | 100 | 13.2 | 54.6 | 67.8 |
| | | 60 | 330 | 100 | 13.3 | 54.6 | 67.9 |
| A12 | $Mo_{10}V_1P_1Re_{0.2}$ | 1 | 330 | 100 | 16.5 | 55.3 | 71.8 |
| | | 60 | 330 | 100 | 16.8 | 55.7 | 72.5 |
| A13 | $Mo_{10}V_1P_1Zr_{0.2}$ | 1 | 335 | 100 | 17.3 | 56.1 | 73.4 |
| | | 60 | 335 | 100 | 17.5 | 56.4 | 73.9 |
| A14 | $Mo_{10}V_1P_1Ce_{0.2}$ | 1 | 330 | 100 | 18.2 | 54.1 | 72.3 |
| | | 60 | 330 | 100 | 19.0 | 54.8 | 73.8 |
| A15 | $Mo_{10}V_1P_1Cr_{0.2}$ | 1 | 330 | 100 | 17.1 | 52.5 | 69.6 |
| | | 60 | 330 | 100 | 17.8 | 53.0 | 70.8 |
| A16 | $Mo_{10}V_1P_1Bi_{0.2}$ | 1 | 330 | 100 | 18.1 | 55.8 | 73.9 |
| | | 60 | 330 | 100 | 18.3 | 56.0 | 74.3 |
| A17 | $Mo_{10}V_1P_1As_{0.2}$ | 1 | 335 | 100 | 18.5 | 56.0 | 74.5 |
| | | 60 | 335 | 100 | 18.5 | 56.6 | 75.1 |

EXAMPLES A18–A22

The dried products as shown in Table A-2 were prepared as in Example A1 and were confirmed to be heteropoly-acid by X-ray diffraction analysis.

The continuous reactions were conducted using the above catalysts in the same reaction conditions as in Example A1. The results are shown in Table A-2.

After the reaction of 60 days, X-ray diffraction analysis of the catalysts was made and it was confirmed that the structure of the catalysts had not changed.

TABLE A-2

| Example | Catalyst composition | Time on stream (days) | Reaction temperature (°C.) | Conversion of isobutyl aldehyde (%) | Yield of methacrolein (%) | Yield of methacrylic acid (%) | Selectivity to (methacrolein + methacrylic acid) (%) |
|---|---|---|---|---|---|---|---|
| A18 | $Mo_{10}V_1P_1Cu_{0.5}$ | 1 | 320 | 100 | 16.1 | 53.5 | 69.6 |
| | | 60 | 320 | 100 | 16.3 | 53.8 | 70.1 |
| A19 | $Mo_{10}V_1P_1Cu_1$ | 1 | 310 | 100 | 13.2 | 51.5 | 64.7 |
| | | 60 | 310 | 100 | 13.3 | 52.5 | 65.8 |
| A20 | $Mo_{10}V_2P_1Cu_{0.3}$ | 1 | 340 | 100 | 14.8 | 55.1 | 69.9 |
| | | 60 | 340 | 100 | 15.2 | 56.6 | 71.8 |
| A21 | $Mo_{10}V_{0.5}P_1Cu_{0.2}$ | 1 | 320 | 100 | 18.0 | 51.1 | 69.1 |
| | | 60 | 320 | 100 | 18.0 | 51.3 | 69.3 |
| A22 | $Mo_{10}V_1P_3Cu_{0.2}$ | 1 | 340 | 100 | 15.0 | 52.5 | 67.5 |

TABLE A-2-continued

| Example | Catalyst composition | Time on stream (days) | Reaction temperature (°C.) | Conversion of isobutyl aldehyde (%) | Yield of methacrolein (%) | Yield of methacrylic acid (%) | Selectivity to (methacrolein + methacrylic acid) (%) |
|---|---|---|---|---|---|---|---|
| | | 60 | 340 | 100 | 15.5 | 53.1 | 68.6 |

EXAMPLE A23

100 g of molybdenum trioxide, 6.3 g of vanadium pentoxide, 1.1 g of copper oxide and 8.0 g of orthophosphoric acid were dispersed or dissolved in 1,000 ml of deionized water and after about 3 hours of heating and stirring of the mixture, 0.45 g of potassium hydroxide was added to the resultant solution. The mixture was refluxed for about 3 hours while boiling. The aqueous solution thus formed was evaporated to dryness on a water bath. The composition of the dried product (the catalyst) was $Mo_{10}V_1P_1Cu_{0.2}K_{0.1}$. In the X-ray diffraction pattern of the catalyst, diffraction peaks of $2\theta=8.0°$, 8.9°, 9.3°, etc. due to heteropoly-acid mainly composed of phosphovanadomolybdic acid and faint diffraction peaks of $2\theta=26.6°$, 10.8°, etc. due to the potassium salt of the heteropoly-acid were recognized. The fact shows that the catalyst obtained is a mixture of heteropoly-acid mainly composed of phosphovanadomolybdic acid and its potassium salt.

The continuous reaction was conducted using the above catalyst in the same reaction conditions as in Example A1. The results are shown in Table A-3.

After the continuous reaction, X-ray diffraction analysis of the catalyst was made and it was confirmed that the structure of the catalyst had not changed.

EXAMPLES A24–A26

0.45 g of potassium hydroxide in Example A23 was replaced in each of the examples with 0.7 g of rubidium hydroxide, 1.0 g of cesium hydroxide, 1.5 g of thallium hydroxide respectively and dried products (catalysts) having compositions as shown in Table A-3 were obtained.

In the X-ray diffraction pattern of the catalysts, diffraction peaks of $2\theta=8.0°$, 8.9°, 9.3°, etc. due to heteropoly-acid mainly composed of phosphovanadomolybdic acid and faint diffraction peaks of $2\theta=26.6°$, 10.8°, etc. due to the salt of the heteropoly-acid were recognized. The fact shows that each of the catalysts is a mixture of heteropoly-acid mainly composed of phosphovanadomolybdid acid and its salt.

A series of continuous reactions were conducted using the above catalysts under the same reaction conditions as in Example A1. The results are as shown in Table A-3.

After the continuous reactions, X-ray diffraction analysis of the catalysts was made and it was confirmed that the structure of the catalysts had not changed.

TABLE A-3

| Example | Catalyst composition | Time on stream (days) | Reaction temperature (°C.) | Conversion of isobutyl aldehyde (%) | Yield of methacrolein (%) | Yield of methacrylic acid (%) | Selectivity to (methacrolein + methacrylic acid) (%) |
|---|---|---|---|---|---|---|---|
| A23 | $Mo_{10}V_1P_1Cu_{0.2}K_{0.1}$ | 1 | 320 | 100 | 19.5 | 58.8 | 78.3 |
| | | 60 | 320 | 100 | 19.5 | 60.0 | 79.5 |
| A24 | $Mo_{10}V_1P_1Cu_{0.2}Rb_{0.1}$ | 1 | 320 | 100 | 18.1 | 58.3 | 76.4 |
| | | 60 | 320 | 100 | 18.0 | 59.3 | 77.3 |
| A25 | $Mo_{10}V_1P_1Cu_{0.2}Cs_{0.1}$ | 1 | 315 | 100 | 19.7 | 59.0 | 78.7 |
| | | 60 | 315 | 100 | 19.9 | 59.5 | 79.4 |
| A26 | $Mo_{10}V_1P_1Cu_{0.2}Tl_{0.1}$ | 1 | 320 | 100 | 18.5 | 58.5 | 77.0 |
| | | 60 | 320 | 100 | 18.7 | 58.8 | 77.5 |

EXAMPLES A27–A42

The dried products (catalysts) as shown in Table A-4 were prepared as in Example A23.

In the X-ray diffraction pattern of the catalysts, diffraction peaks of $2\theta=8.0°$, 8.9°, 9.3°, etc. due to heteropoly-acid mainly composed of phosphovanadomolybdic acid and faint diffraction peaks of $2\theta=26.6°$, 10.8°, etc. due to the salt of heteropoly-acid were recognized. The fact shows that each of the catalysts is a mixture of heteropoly-acid mainly composed of phosphovanadomolybdic acid and its salt.

A series of continuous reactions were conducted using the above catalysts under the same reaction conditions as in Example A1. The results are as shown in Table A-4.

After the continuous reactions, X-ray diffraction analysis of the catalysts was made and it was confirmed that the structure of the catalysts had not changed.

TABLE A-4

| Example | Catalyst composition | Time on stream (days) | Reaction temperature (°C.) | Conversion of isobutyl aldehyde (%) | Yield of methacrolein (%) | Yield of methacrylic acid (%) | Selectivity to (methacrolein + methacrylic acid) (%) |
|---|---|---|---|---|---|---|---|
| A27 | $Mo_{10}V_1P_1Sn_{0.2}K_{0.1}$ | 1 | 325 | 100 | 16.7 | 54.8 | 71.5 |
| | | 60 | 325 | 100 | 16.9 | 55.0 | 71.9 |
| A28 | $Mo_{10}V_1P_1Th_{0.2}K_{0.1}$ | 1 | 330 | 100 | 15.5 | 55.1 | 70.6 |
| | | 60 | 330 | 100 | 15.8 | 55.3 | 71.1 |
| A29 | $Mo_{10}V_1P_1Al_{0.2}K_{0.1}$ | 1 | 330 | 100 | 16.0 | 56.1 | 72.1 |
| | | 60 | 330 | 100 | 16.2 | 56.3 | 72.5 |
| A30 | $Mo_{10}V_1P_1Ge_{0.2}K_{0.1}$ | 1 | 325 | 100 | 15.5 | 56.2 | 71.7 |
| | | 60 | 325 | 100 | 15.8 | 56.6 | 72.4 |
| A31 | $Mo_{10}V_1P_1Ni_{0.2}K_{0.1}$ | 1 | 325 | 100 | 17.5 | 54.8 | 72.3 |

TABLE A-4-continued

| Example | Catalyst composition | Time on stream (days) | Reaction temperature (°C.) | Conversion of isobutyl aldehyde (%) | Yield of methacrolein (%) | Yield of methacrylic acid (%) | Selectivity to (methacrolein + methacrylic acid) (%) |
|---|---|---|---|---|---|---|---|
| | | 60 | 325 | 100 | 17.0 | 55.5 | 72.5 |
| A32 | $Mo_{10}V_1P_1Fe_{0.2}K_{0.1}$ | 1 | 325 | 100 | 16.8 | 54.0 | 70.8 |
| | | 60 | 325 | 100 | 16.9 | 54.5 | 71.4 |
| A33 | $Mo_{10}V_1P_1Co_{0.2}K_{0.1}$ | 1 | 325 | 100 | 17.0 | 54.5 | 71.5 |
| | | 60 | 325 | 100 | 17.3 | 54.8 | 72.1 |
| A34 | $Mo_{10}V_1P_1Zn_{0.2}K_{0.1}$ | 1 | 330 | 100 | 18.5 | 52.1 | 70.6 |
| | | 60 | 330 | 100 | 18.7 | 52.3 | 71.0 |
| A35 | $Mo_{10}V_1P_1Ti_{0.2}K_{0.1}$ | 1 | 325 | 100 | 17.0 | 54.9 | 71.9 |
| | | 60 | 325 | 100 | 17.5 | 55.1 | 72.6 |
| A36 | $Mo_{10}V_1P_1Pb_{0.2}K_{0.1}$ | 1 | 325 | 100 | 14.5 | 54.5 | 69.0 |
| | | 60 | 325 | 100 | 14.8 | 54.8 | 69.6 |
| A37 | $Mo_{10}V_1P_1Re_{0.2}K_{0.1}$ | 1 | 325 | 100 | 15.8 | 56.5 | 72.3 |
| | | 60 | 325 | 100 | 16.0 | 57.0 | 73.0 |
| A38 | $Mo_{10}V_1P_1Zr_{0.2}K_{0.1}$ | 1 | 330 | 100 | 17.5 | 56.5 | 74.0 |
| | | 60 | 330 | 100 | 17.0 | 57.3 | 74.3 |
| A39 | $Mo_{10}V_1P_1Ce_{0.2}K_{0.1}$ | 1 | 325 | 100 | 18.5 | 54.5 | 73.0 |
| | | 60 | 325 | 100 | 18.6 | 55.0 | 73.6 |
| A40 | $Mo_{10}V_1P_1Cr_{0.2}K_{0.1}$ | 1 | 325 | 100 | 17.3 | 53.5 | 70.8 |
| | | 60 | 325 | 100 | 17.5 | 53.7 | 71.2 |
| A41 | $Mo_{10}V_1P_1Bi_{0.2}K_{0.1}$ | 1 | 325 | 100 | 19.5 | 55.8 | 75.3 |
| | | 60 | 325 | 100 | 19.4 | 56.1 | 75.5 |
| A42 | $Mo_{10}V_1P_1As_{0.2}K_{0.1}$ | 1 | 330 | 100 | 19.8 | 56.2 | 76.0 |
| | | 60 | 330 | 100 | 19.5 | 57.0 | 76.5 |

EXAMPLES A43–A45

The dried products (catalysts) as shown in Table A-5 were prepared as in Example A1 and were confirmed to be heteropoly-acid by X-ray diffraction analysis.

The continuous reactions were conducted using the above catalysts in the same reaction conditions as in Example A1. The results are shown in Table A-5.

After the continuous reactions, X-ray diffraction analysis of the catalysts was made and it was confirmed that the structure of the catalysts had not changed.

TABLE A-5

| Example | Catalyst composition | Time on stream (days) | Reaction temperature (°C.) | Conversion of isobutyl aldehyde (%) | Yield of methacrolein (%) | Yield of methacrylic acid (%) | Selectivity to (methacrolein + methacrylic acid) (%) |
|---|---|---|---|---|---|---|---|
| A43 | $Mo_{10}V_1P_1Ge_{0.2}Sn_{0.2}$ | 1 | 330 | 100 | 17.1 | 55.5 | 72.6 |
| | | 60 | 330 | 100 | 17.0 | 55.8 | 72.8 |
| A44 | $Mo_{10}V_1P_1Fe_{0.2}Zr_{0.1}$ | 1 | 330 | 100 | 18.0 | 56.3 | 74.3 |
| | | 60 | 330 | 100 | 17.5 | 56.9 | 74.4 |
| A45 | $Mo_{10}V_1P_1Ni_{0.2}As_{0.2}$ | 1 | 330 | 100 | 18.7 | 56.6 | 75.3 |
| | | 60 | 330 | 100 | 18.6 | 57.1 | 75.7 |
| A46 | $Mo_{10}V_1P_1Bi_{0.1}As_{0.2}K_{0.2}$ | 1 | 325 | 100 | 19.9 | 56.6 | 76.5 |
| | | 60 | 325 | 100 | 20.0 | 57.0 | 77.0 |
| A47 | $Mo_{10}V_1P_1Fe_{0.2}Zr_{0.1}K_{0.1}$ | 1 | 320 | 100 | 18.0 | 56.5 | 74.5 |
| | | 60 | 320 | 100 | 17.5 | 58.1 | 75.6 |
| A48 | $Mo_{10}V_1P_1Fe_{0.2}Ce_{0.1}K_{0.1}$ | 1 | 325 | 100 | 18.7 | 54.8 | 73.5 |
| | | 60 | 325 | 100 | 18.5 | 55.5 | 74.0 |
| A49 | $Mo_{10}V_1P_1Ni_{0.2}As_{0.2}K_{0.1}$ | 1 | 325 | 100 | 20.2 | 56.9 | 77.1 |
| | | 60 | 325 | 100 | 20.5 | 57.1 | 77.6 |
| A50 | $Mo_{10}V_1P_1Sn_{0.2}As_{0.2}Cs_{0.1}$ | 1 | 325 | 100 | 19.8 | 56.5 | 76.3 |
| | | 60 | 325 | 100 | 19.7 | 56.9 | 76.6 |
| A51 | $Mo_{10}V_1P_1Zr_{0.2}As_{0.2}Cs_{0.2}$ | 1 | 325 | 100 | 19.5 | 57.1 | 76.6 |
| | | 90 | 325 | 100 | 19.0 | 57.8 | 76.8 |
| A52 | $Mo_{10}V_1P_1Cu_{0.2}K_{0.1}Cs_{0.1}$ | 1 | 320 | 100 | 19.9 | 59.5 | 79.4 |
| | | 60 | 320 | 100 | 19.5 | 60.0 | 79.5 |

EXAMPLES A46–A52

The dried products (catalysts) as shown in Table A-5 were prepared as in Example A23 and were confirmed to be a mixture of heteropoly-acid mainly composed of phosphovanadomolybdic acid and its salt by X-ray diffraction analysis.

The continuous reactions were conducted using the above catalysts in the same reaction conditions as in Example A1. The results are shown in Table A-5.

After the continuous reactions, X-ray diffraction analysis of the catalysts was made and it was confirmed that the structure of the catalysts had not changed.

EXAMPLE A53

The oxidation of isobutyl aldehyde was carried out in a similar manner as in Example A1 except that the reaction temperature was changed. The results are shown in Table A-6.

TABLE A-6

| Reaction temperature (°C.) | Conversion of isobutyl aldehyde (%) | Yield of methacrolein (%) | Yield of methacrylic acid (%) | Selectivity to (methacrolein + methacrylic acid) (%) |
|---|---|---|---|---|
| 325 | 100 | 19.6 | 58.0 | 77.6 |
| 300 | 100 | 36.0 | 44.5 | 80.5 |
| 275 | 100 | 60.2 | 25.2 | 85.4 |

TABLE A-6-continued

| Reaction temperature (°C.) | Conversion of isobutyl aldehyde (%) | Yield of methacrolein (%) | Yield of methacrylic acid (%) | Selectivity to (methacrolein + methacrylic acid) (%) |
|---|---|---|---|---|
| 240 | 100 | 81.0 | 6.7 | 87.7 |

EXAMPLE B1

100 g of molybdenum trioxide, 6.3 g of vanadium pentoxide, 1.1 g of copper oxide, 8.0 g of orthophosphoric acid and 1.9 g of arsenic acid were dispersed or dissolved into 1000 ml of deionized water. The resultant mixture was boiled and refluxed with stirring for about 6 hours to produce a clear orange red solution. After removing a slight amount of insoluble contents, it was evaporated to dryness on a hot bath. The dried product thus obtained (catalyst) had a composition: $Mo_{10}V_1P_1Cu_{0.2}As_{0.2}$ and were confirmed to be heteropoly-acid by the observation of X-ray diffraction peaks at $2\theta = 8.0°, 8.9°, 9.3°$ and the like. It was ground to 24–48 mesh and diluted with the same amount of quartz sands having the same size in mesh and then charged into a tubular reactor made of glass of 18 mm in inside diameter and the reactor was immersed in a fluidized bath. The feed gas of a composition wherein isobutyl aldehyde:oxygen:nitrogen:water vapour = 1:2.5:10:7 (in molar ratio) was passed through the tubular reactor at $SV = 1500 \text{ hr}^{-1}$ (NTP standard) and subjected to oxidation reaction at a reaction temperature of 330° C. for 60 days. The results are shown in Table B-1.

After the reaction of 60 days, the X-ray diffraction analysis of the catalyst was made and it was confirmed that molybdenum trioxide had not been formed and the structure of the catalyst had not changed.

EXAMPLES B2–B16

1.9 g of arsenic acid in Example B1 was replaced in each of the examples with 3.7 g of thorium oxide, 0.72 g of aluminum oxide, 1.4 g of germanium oxide, 1.0 g of nickel oxide, 1.1 g of iron oxide, 1.1 g of tricobalt tetroxide, 1.1 g of zinc oxide, 1.1 g of titanium oxide, 3.2 g of trilead tetroxide, 3.4 g of rhenium heptoxide, 3.2 g of zirconium oxide, 2.4 g of cerium oxide, 3.2 g of bismuth oxide, 2.1 g of tin oxide and 1.4 g of chromium oxide respectively and dried products (catalysts) having compositions as shown in Table B-1 were obtained. The dried products thus obtained were confirmed to be heteropoly-acid by the observation of X-ray diffraction peaks at $2\theta = 8.0°, 8.9°, 9.3°$ and the like.

The continuous reactions were conducted using the above catalysts under the same reaction conditions as in Example B1. The results are as shown in Table B-1.

After the reaction of 60 days, X-ray diffraction analysis of the catalysts was made and it was confirmed that the structure of the catalysts had not changed.

TABLE B-1

| Example | Catalyst composition | Time on stream (days) | Reaction temperature (°C.) | Conversion of isobutyl aldehyde (%) | Yield of methacrolein (%) | Yield of methacrylic acid (%) | Selectivity to (methacrolein + methacrylic acid) (%) |
|---|---|---|---|---|---|---|---|
| B1 | $Mo_{10}V_1P_1Cu_{0.2}As_{0.2}$ | 1 | 330 | 100 | 19.1 | 64.1 | 83.2 |
| | | 60 | 330 | 100 | 19.5 | 64.9 | 84.4 |
| B2 | $Mo_{10}V_1P_1Cu_{0.2}Th_{0.2}$ | 1 | 330 | 100 | 19.6 | 61.8 | 81.4 |
| | | 60 | 330 | 100 | 19.3 | 62.2 | 81.5 |
| B3 | $Mo_{10}V_1P_1Cu_{0.2}Al_{0.2}$ | 1 | 330 | 100 | 18.5 | 62.9 | 81.4 |
| | | 60 | 330 | 100 | 18.8 | 63.5 | 82.3 |
| B4 | $Mo_{10}V_1P_1Cu_{0.2}Ge_{0.2}$ | 1 | 325 | 100 | 19.8 | 61.8 | 81.6 |
| | | 60 | 325 | 100 | 20.2 | 62.2 | 82.4 |
| B5 | $Mo_{10}V_1P_1Cu_{0.2}Ni_{0.2}$ | 1 | 325 | 100 | 19.3 | 61.8 | 81.1 |
| | | 60 | 325 | 100 | 19.0 | 62.9 | 81.9 |
| B6 | $Mo_{10}V_1P_1Cu_{0.2}Fe_{0.2}$ | 1 | 325 | 100 | 18.3 | 62.7 | 81.0 |
| | | 60 | 325 | 100 | 17.5 | 64.0 | 81.5 |
| B7 | $Mo_{10}V_1P_1Cu_{0.2}Co_{0.2}$ | 1 | 325 | 100 | 18.1 | 62.4 | 80.5 |
| | | 60 | 325 | 100 | 18.0 | 62.9 | 80.9 |
| B8 | $Mo_{10}V_1P_1Cu_{0.2}Zn_{0.2}$ | 1 | 330 | 100 | 19.9 | 61.0 | 80.9 |
| | | 60 | 330 | 100 | 19.9 | 61.4 | 81.3 |
| B9 | $Mo_{10}V_1P_1Cu_{0.2}Ti_{0.2}$ | 1 | 325 | 100 | 18.6 | 62.3 | 80.9 |
| | | 60 | 325 | 100 | 19.0 | 62.7 | 81.7 |
| B10 | $Mo_{10}V_1P_1Cu_{0.2}Pb_{0.2}$ | 1 | 325 | 100 | 18.3 | 62.7 | 81.0 |
| | | 60 | 325 | 100 | 18.0 | 63.7 | 81.7 |
| B11 | $Mo_{10}V_1P_1Cu_{0.2}Re_{0.2}$ | 1 | 325 | 100 | 19.7 | 62.0 | 81.7 |
| | | 60 | 325 | 100 | 19.5 | 63.0 | 82.5 |
| B12 | $Mo_{10}V_1P_1Cu_{0.2}Zr_{0.2}$ | 1 | 330 | 100 | 19.1 | 62.2 | 81.3 |
| | | 60 | 330 | 100 | 19.0 | 63.0 | 82.0 |
| B13 | $Mo_{10}V_1P_1Cu_{0.2}Ce_{0.2}$ | 1 | 325 | 100 | 19.6 | 61.9 | 81.5 |
| | | 60 | 325 | 100 | 19.5 | 62.5 | 82.0 |
| B14 | $Mo_{10}V_1P_1Cu_{0.2}Bi_{0.2}$ | 1 | 325 | 100 | 18.5 | 62.5 | 81.0 |
| | | 60 | 325 | 100 | 18.0 | 63.7 | 81.7 |
| B15 | $Mo_{10}V_1P_1Cu_{0.2}Sn_{0.2}$ | 1 | 325 | 100 | 19.6 | 62.0 | 81.6 |
| | | 60 | 325 | 100 | 19.9 | 61.4 | 81.3 |
| B16 | $Mo_{10}V_1P_1Cu_{0.2}Cr_{0.2}$ | 1 | 325 | 100 | 19.0 | 61.8 | 80.8 |
| | | 60 | 325 | 100 | 19.2 | 63.1 | 82.3 |

EXAMPLE B17

100 g of molybdenum trioxide, 6.3 g of vanadium pentoxide, 1.1 g of copper oxide, 1.9 g of arsenic acid and 8.0 g of orthophosphoric acid were dispersed or dissolved in 1000 ml of deionized water and after about 3 hours of heating and stirring of the mixture, 0.45 g of potassium hydroxide was added to the resultant solution. The mixture was refluxed for about 3 hours while boiling. The aqueous solution thus formed was evaporated to dryness on a water bath. The composition of the dried product (the catalyst) was $Mo_{10}V_1P_1Cu_{0.2}As_{0.2}K_{0.1}$. In the X-ray diffraction pattern of the catalyst, diffraction peaks of $2\theta = 8.0°, 8.9°, 9.3°$, etc. due to heteropoly-acid mainly composed of phosphovanadomolybdic acid and faint diffraction peaks of $2\theta=26.6°$, $10.8°$, etc. due to the potassium salt of the heteropoly-acid were recognized. The fact shows that the catalyst obtained is a mixture of heteropoly-acid mainly composed of phosphovanadomolybdic acid and its salt.

The continuous reaction was conducted using the above catalyst in the same reaction conditions as in Example B1. The results are shown in Table B-2.

After the continuous reaction, X-ray diffraction analysis of the catalyst was made and it was confirmed that the structure of the catalyst had not changed.

EXAMPLES B18–B20

0.45 g of potassium hydroxide in Example B17 was replaced in each of the examples with 0.7 g of rubidium hydroxide, 1.0 g of cesium hydroxide, 1.5 g of thallium hydroxide respectively and dried products (catalysts) having compositions as shown in Table B-2 were obtained.

catalysts is a mixture of heteropoly-acid mainly composed of phosphovanadomolybdic acid and its salt.

The continuous reactions were conducted using the above catalysts under the same reaction conditions as in Example B1. The results are shown in Table B-2.

After the continuous reactions, X-ray diffraction analysis of the catalysts was made and it was confirmed that the structure of the catalysts had not changed.

TABLE B-2

| Example | Catalyst composition | Time on stream (days) | Reaction temperature (°C.) | Conversion of isobutyl aldehyde (%) | Yield of methacrolein (%) | Yield of methacrylic acid (%) | Selectivity to (methacrolein + methacrylic acid) (%) |
|---|---|---|---|---|---|---|---|
| B17 | $Mo_{10}V_1P_1Cu_{0.2}As_{0.2}K_{0.1}$ | 1 | 325 | 100 | 19.1 | 64.6 | 83.7 |
|  |  | 60 | 325 | 100 | 19.6 | 65.0 | 84.6 |
| B18 | $Mo_{10}V_1P_1Cu_{0.2}As_{0.2}Rb_{0.1}$ | 1 | 325 | 100 | 18.9 | 64.9 | 83.8 |
|  |  | 60 | 325 | 100 | 18.5 | 65.7 | 84.2 |
| B19 | $Mo_{10}V_1P_1Cu_{0.2}As_{0.2}Cs_{0.1}$ | 1 | 320 | 100 | 19.1 | 65.3 | 84.4 |
|  |  | 60 | 320 | 100 | 19.0 | 65.9 | 84.9 |
| B20 | $Mo_{10}V_1P_1Cu_{0.2}As_{0.2}Tl_{0.1}$ | 1 | 325 | 100 | 18.3 | 64.8 | 83.1 |
|  |  | 60 | 325 | 100 | 18.1 | 65.2 | 83.3 |

EXAMPLES B21–B25

The dried products (catalysts) as shown in Table B-3 were prepared as in Example B17 and were confirmed to be a mixture of heteropoly-acid mainly composed of phosphovanadomolybdic acid and its salt by X-ray diffraction analysis.

The continuous reactions were conducted using the above catalysts in the same reaction conditions as in Example B1. The results are shown in Table B-3.

After the continuous reactions, X-ray diffraction analysis of the catalysts was made and it was confirmed that the structure of the catalysts had not changed.

TABLE B-3

| Example | Catalyst composition | Time on stream (days) | Reaction temperature (°C.) | Conversion of isobutyl aldehyde (%) | Yield of methacrolein (%) | Yield of methacrylic acid (%) | Selectivity (methacrolein + methacrylic acid) (%) |
|---|---|---|---|---|---|---|---|
| B21 | $Mo_{10}V_1P_1Cu_{0.2}Sn_{0.1}Al_{0.1}K_{0.1}$ | 1 | 330 | 100 | 19.5 | 61.7 | 81.2 |
|  |  | 60 | 330 | 100 | 19.4 | 62.5 | 81.9 |
| B22 | $Mo_{10}V_1P_1Cu_{0.2}Ni_{0.1}Ge_{0.1}K_{0.1}$ | 1 | 325 | 100 | 19.0 | 62.6 | 81.6 |
|  |  | 60 | 325 | 100 | 19.0 | 63.1 | 82.1 |
| B23 | $Mo_{10}V_1P_1Cu_{0.2}As_{0.1}Re_{0.1}K_{0.1}$ | 1 | 330 | 100 | 19.3 | 64.3 | 83.6 |
|  |  | 60 | 330 | 100 | 19.7 | 64.8 | 84.5 |
| B24 | $Mo_{10}V_1P_1Cu_{0.2}Sn_{0.1}K_{0.1}Cs_{0.1}$ | 1 | 320 | 100 | 19.7 | 61.7 | 81.4 |
|  |  | 60 | 320 | 100 | 19.6 | 62.0 | 81.6 |
| B25 | $Mo_{10}V_1P_1Cu_{0.2}Co_{0.1}Cs_{0.1}Rb_{0.1}$ | 1 | 320 | 100 | 19.2 | 61.8 | 81.0 |
|  |  | 60 | 320 | 100 | 19.0 | 62.5 | 81.5 |

In the X-ray diffraction pattern of the catalysts, diffraction peaks of $2\theta=8.0°$, $8.9°$, $9.3°$, etc. due to heteropoly-acid mainly composed of phosphovanadomolybdic acid and faint diffraction peaks of $2\theta=26.6°$, $10.8°$, etc. due to the salt of the heteropoly-acid were recognized. The fact shows that each of the

EXAMPLES B26–B29

The dried products (catalysts) as shown in Table B-4 were prepared as in Example B1 or Example B17.

The continuous reactions were conducted using the above catalysts in the same reaction conditions as in Example B1. The results are shown in Table B-4.

TABLE B-4

| Example | Catalyst composition | Time on stream (days) | Reaction temperature (°C.) | Conversion of isobutyl aldehyde (%) | Yield of methacrolein (%) | Yield of methacrylic acid (%) | Selectivity (methacrolein + methacrylic acid) (%) |
|---|---|---|---|---|---|---|---|
| B26 | $Mo_{10}V_1P_1Cu_{0.5}As_{0.5}K_{0.1}$ | 1 | 340 | 100 | 20.3 | 60.8 | 81.1 |
|  |  | 60 | 340 | 100 | 20.1 | 61.1 | 81.2 |
| B27 | $Mo_{10}V_1P_1Cu_{1.0}As_{0.8}K_{0.1}$ | 1 | 330 | 100 | 21.1 | 59.9 | 81.0 |
|  |  | 60 | 330 | 100 | 21.1 | 60.0 | 81.1 |
| B28 | $Mo_{10}V_{0.5}P_1Cu_{0.2}As_{0.2}$ | 1 | 335 | 100 | 18.9 | 64.8 | 83.7 |
|  |  | 60 | 335 | 100 | 18.8 | 65.1 | 83.9 |
| B29 | $Mo_{10}V_1P_3Cu_{0.2}As_{0.2}K_{0.3}$ | 1 | 330 | 100 | 19.7 | 61.3 | 81.0 |

TABLE B-4-continued

| Example | Catalyst composition | Time on stream (days) | Reaction temperature (°C.) | Conversion of isobutyl aldehyde (%) | Yield of methacrolein (%) | Yield of methacrylic acid (%) | Selectivity (methacrolein + methacrylic acid) (%) |
|---|---|---|---|---|---|---|---|
| | | 60 | 330 | 100 | 19.5 | 62.0 | 81.5 |

EXAMPLES B30–B31

With use of the catalyst of Example B17 the oxidation of isobutyl aldehyde was carried out in a similar manner as in Example B1 except that the space velocity (SV) was changed. The results are shown in Table B-5. These results show that the increase in the space velocity (SV) has no substantial effect on the results of the reaction.

TABLE B-5

| Example | Catalyst composition | SV (hr$^{-1}$) | Reaction temperature (°C.) | Conversion of isobutyl aldehyde (%) | Yield of methacrolein (%) | Yield of methacrylic acid (%) | Selectivity (methacrolein + methacrylic acid) (%) |
|---|---|---|---|---|---|---|---|
| B30 | $Mo_{10}V_1P_1Cu_{0.2}As_{0.2}K_{0.1}$ | 500 | 315 | 100 | 18.2 | 64.9 | 83.1 |
| B31 | $Mo_{10}V_1P_1Cu_{0.2}As_{0.2}K_{0.1}$ | 3000 | 340 | 100 | 18.5 | 63.8 | 82.3 |

COMPARATIVE EXAMPLE 1

Dried product having a composition $Mo_{10}V_1P_1$ was obtained in the same manner as in Example A1 but with no addition of 1.1 g of copper oxide and using the above catalyst the continuous reaction was carried out in a similar manner as in Example A1. The results are shown in Table C-1.

COMPARATIVE EXAMPLE 2

A catalyst was prepared in the same manner as in Example A23, however, instead of 0.45 g of potassium hydroxide, 9 g of potassium hydroxide was used to obtain a catalyst of the composition of $Mo_{10}V_1P_1Cu_{0.2}K_2$. Oxidation of isobutyl aldehyde was carried out using the catalyst thus obtained under the same conditions as in Example A1. The results are shown in Table C-1. Since activity of the catalyst was low, it was necessary to raise a reaction temperature, and the yield was low. Examination of the catalyst by X-ray diffraction showed that the potassium salt of heteropoly-acid predominated in the catalyst.

COMPARATIVE EXAMPLE 3–4

The dried products (catalysts) as shown in Table C-1 were prepared as in Comparative Example 2 and the continuous reactions were conducted in the same reaction conditions as in Example A1. The results are shown in Table C-1.

What is claimed is:

1. A process for producing methacrolein and methacrylic acid by oxidizing isobutyl aldehyde with molecular oxygen or molecular oxygen-containing gas in the vapor phase characterized by the use of a catalyst of heteropoly-acid or a mixture of heteropoly-acid and its salt which has the general formula:

$$Mo_{a'}V_{b'}P_{c'}Cu_{d'}X'_{e'}Y'_{f'}O_{g'},$$

wherein, Mo, V, P, Cu and O represent respectively molybdenum, vanadium, phosphorus, copper and oxygen, X' represents one or more elements selected from the group consisting of arsenic, thorium, aluminum, germanium, nickel, iron, cobalt, zinc, titanium, lead, rhenium, zirconium, cerium, bismuth, tin and chromium, Y' represents one or more elements selected from the group consisting of potassium, rubidium, cesium and thallium and a', b', c', d', e', f' and g' represent the atomic ratio of the elements where,
  a' is 10,
  b' is a number of 6 or less than 6 excluding 0,
  c' is a number of 0.5 to 6,
  d' is a number of 3 or less than 3 excluding 0,
  e' is a number of 3 or less than 3 excluding 0,
  d'+e' is a number of 3 or less than 3 excluding 0,
  f' is a number of 0 to 0.8,
  g' is a number determined depending on the valency and atomic ratio of other elements.

2. The process of claim 1, wherein a' is 10, b' is a number of 0.5 to 3, c' is a number of 0.5 to 3, d' is a number of 0.01 to 1.0, e' is a number of 0.01 to 1.0, f' is a number of 0 to 0.5.

3. The process of claim 1, wherein reaction temperature is between 250° and 400° C.

4. The process of claim 1, wherein the reaction is carried out in the presence of water vapor.

* * * * *

TABLE C-1

| Comparative Example | Catalyst composition | Time on stream (days) | Reaction temperature (°C.) | Conversion of isobutyl aldehyde (%) | Yield of methacrolein (%) | Yield of methacrylic acid (%) | Selectivity to (methacrolein + methacrylic acid) (%) |
|---|---|---|---|---|---|---|---|
| 1 | $Mo_{10}V_1P_1$ | 1 | 340 | 100 | 15.8 | 45.0 | 60.8 |
| | | 30 | 340 | 100 | 17.0 | 42.5 | 59.5 |
| 2 | $Mo_{10}V_1P_1Cu_{0.2}K_2$ | 1 | 350 | 100 | 17.1 | 48.8 | 65.9 |
| | | 30 | 350 | 100 | 18.8 | 45.1 | 63.9 |
| 3 | $Mo_{10}V_1P_1Ge_{0.2}Cs_2$ | 1 | 350 | 100 | 20.2 | 39.8 | 60.0 |
| | | 30 | 350 | 100 | 21.8 | 36.1 | 57.9 |
| 4 | $Mo_{10}V_1P_1Ni_{0.2}As_{0.2}K_2$ | 1 | 350 | 100 | 19.7 | 42.1 | 61.8 |
| | | 30 | 350 | 100 | 21.1 | 38.3 | 59.4 |